Figure 1:
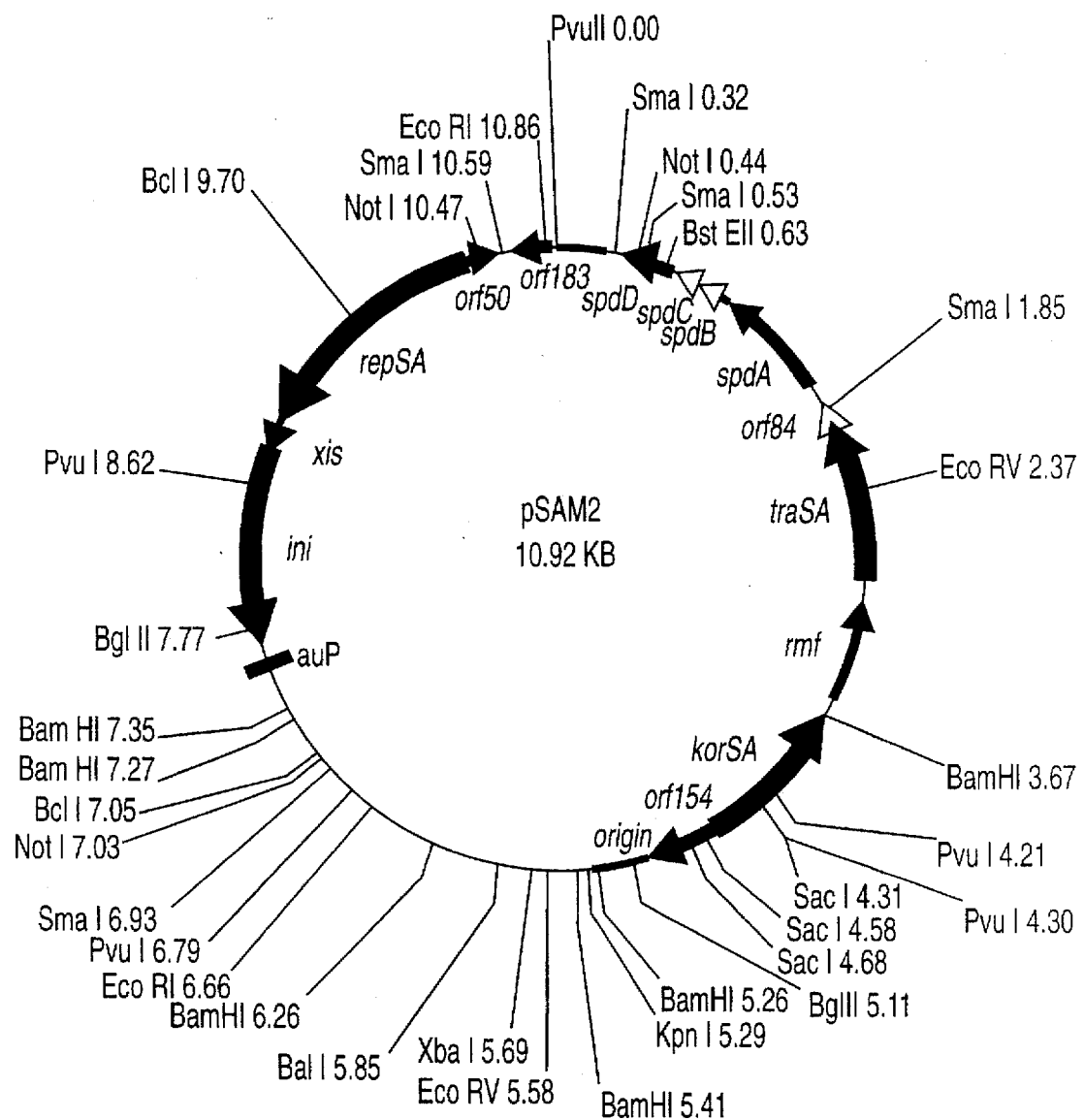

United States Patent [19]

Friedmann et al.

[11] Patent Number: 5,741,675
[45] Date of Patent: Apr. 21, 1998

US005741675A

[54] REGULATORY NUCLEIC ACID SEQUENCES AND USES IN ACTINOMYCETES

[75] Inventors: Annick Friedmann, Villiers-le-Bacle; Michel Guerineau, Paris; Juliette Hagege, Orsay; Jean-Luc Pernodet, Cachan; Guënnady Sezonov, Paris, all of France

[73] Assignee: Rhone-Poulenc Rorer S.A., Antony, France

[21] Appl. No.: 656,253

[22] PCT Filed: Dec. 5, 1994

[86] PCT No.: PCT/FR94/01413

§ 371 Date: Jun. 7, 1996

§ 102(e) Date: Jun. 7, 1996

[87] PCT Pub. No.: WO95/16046

PCT Pub. Date: Jun. 15, 1995

[30] Foreign Application Priority Data

Dec. 8, 1993 [FR] France ................................ 93 14701

[51] Int. Cl.$^6$ .............................. C12N 1/21; C12N 15/31; C12N 15/76; C12P 21/00
[52] U.S. Cl. .................. 435/69.1; 435/172.3; 435/252.3; 435/320.1; 536/23.1; 536/23.7
[58] Field of Search ........................... 435/320.1, 69.1, 435/172.3, 252.3; 536/23.7, 23.1

[56] References Cited

FOREIGN PATENT DOCUMENTS

| 0 346 000 | 12/1989 | European Pat. Off. . |
| 0 350 341 | 10/1990 | France . |
| WO 94/08014 | 4/1994 | France . |

OTHER PUBLICATIONS

Bibb et al., Cloning and analysis of the promoter region of the erythromycin-resistance gene (ermE) of *Streptomyces erythraeus* Gene 41 (1986).

Pernodet et al., Organization and nucleotide sequence analysis of a ribosomal RNA gene cluster from *Streptomyces ambofaciens* Gene 79 (1989).

Murakami et al, "Thiostrepton–Induced Gene Expression in *Streptomyces lividans*" J. Bact., 171 (1989).

Mazodier et al., "Characterization of the groEl–Like Genes in *Streptomyces albus*" J. Bact. 173 (1991).

Smokvina et al, Applications of the intergrated plasmid pSAM2, GIM90, Proceedings, vol. 1, pp. 403–407.

Smokvina et al., "Construction of a series of pSAM2–based integrative vectors for use in actinomycetes" Gene 94 (1990).

Maniatis T. et all., "Molecular Cloning, a Laboratory Manual", Cold Spring Harbor Laboratory, Cold Spring Harbor, N.Y., 1982.

Ausubel F.M. et al. (eds), "Current Protocols in Molecular Biology", John Wiley & Sons, New York (1987).

Taylor et al., The use of phosphorothiate–modified DNA in restriction enzyme reactions to prepare nicked DNA Nucleic Acids Rs. 13 (1985).

Saiki, R., K., et al. "Enzymatic Amplification of β–Globin Genomic Sequences and Restriction Site Analysis for Diagnosis of Sickle Cell Anemia" Science 230 (1985) 1350–1354.

Mullis K.B. and Faloona F.A., Specific Synthesis of DNA in Vitro via a Polymerase–Catalyzed Chain Reaction Enzym. 155 (1987).

Sanger et al, "DNA sequencing with chain–terminating inhibitors" Proc. Natl. Acad. Sci. USA, 74 5463–5467 (1977).

Hopwood et al, Plasmids, Recomibnation and Chromosome Mapping in *Streptomyces lividans* 66; J. Gen. Microbiol. 129 (1983).

Ward et al., "Construction and characterisation of a series of multi–copy promoter–probe plasmid vectors for Streptomyces using the aminoglycoside phosphotransferase gene from Tn5 as indicator" Mol. Gen. Genet. 203 (1986).

Hagege et al., Plasmid 31:2 (1994).

Hagege et al., J. of Bact. 175:17 (1993).

Sokvina et al., Plasmid 25:(1) (1991) pp. 40–52.

Labes et al., Sixth DFGWT/AFAST, 27–30/11/92.

Pernodet el al., Mol. Gen. Genet. 198:35–41 (1984).

*Primary Examiner*—Johnny F. Railey, II
*Attorney, Agent, or Firm*—Finnegan, Henderson, Farabow, Garrett & Dunner, L.L.P.

[57] ABSTRACT

Novel nucleic acid sequences, vectors for expressing same, and uses of said sequences, in particular in actinomycetes fermentation methods.

16 Claims, 7 Drawing Sheets

|  | Promoter RBS | rmf gene | APPEARANCE OF THE FREE FORM OF pSAM2 |
|---|---|---|---|
| pIJ487 | — | | no |
| pOS541 | ermE* +1 +53 | +563 | yes pSAM2(B2) |
| pOS531 | | | no |
| pOS532 | ermF* | | no |
| pOS544 | | BspHI (Klenow) | no |
| pOS666 | tip A | | yes pOS666 |

*FIG. 7*

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
      ( A ) LENGTH: 812 base pairs
      ( B ) TYPE: nucleic acid
      ( C ) STRANDEDNESS: single
      ( D ) TOPOLOGY: linear ( i i ) MOLECULE TYPE: DNA (genomic)

( x i ) SEQUENCE DESCRIPTION: SEQ ID NO:1:

```
CCAGCAGCCG  ACTGACGACC  GCTCAACTCC  TCACAGCCCG  TCGCGAGTTC  TCTGTCGCGG     60

CGGGTTGACT  CATGTATAGG  AGTGGTGCAC  TCTTCTTCAT  GTCACTCATA  TACATGAGTG    120

ACGGAGTCCA  GCCTCTATAG  AGGAGTGATC  CGCTGTGCGT  CAGATCCCCG  TCGACACCTC    180

CGCCGCAACC  GTGATGGTCG  CCAAGACTCC  GGAGCCGAAG  GTGAAGGACC  GCCGGACCGG    240

TGAGCTGGCC  GTCGACGCCG  AGACCGGTGC  CAAGCTCATG  ACCGTGAACG  TGATGTTCGC    300

GGCCAACGAC  GAAGTCGAGA  TTCTGTCCGT  GACCGTCCCG  GAGACCGGTA  TCTCCGGTGA    360

ACTGGCCATG  GGTACCCCGG  TCGCGCTGAC  GGGGCTCATC  GCCCGGCCGT  GGGAGAACGA    420

GTTCAACGGC  CAGAAGCGGC  ACGGCATCGC  GTTCCGCGCG  GTCGCGGTCA  CGTCGCTGAC    480

CGCTGCGGGC  TCGAAGGCTG  CCTGATCATG  ACGTGGTTCA  TGGTCGCTGT  GGTTGTGGTC    540

GTCGCTGCTG  CGGGTCTCCT  GCGGTGGCGG  CGCCCCGCCT  GGTACTGGCT  CACCTTCGGG    600

GCCCTGGTCG  CGACGGTGCG  GGTCCTGGTC  CGTACGCCTC  GGTCATGGAA  GCGTGCGGGC    660

TGACGGTCCG  CCCTCACGCT  GGCGGCTGCT  CTGGCCCGGA  TGGCGAATGC  CGCGCCTGAG    720

TCCCGGCCGC  CGCGCATCTT  GCGGTTACGT  CCCACTCGTA  CCGGCCTGGT  CTGCGGCTCA    780

AGCTCCGGCC  GGGACAGGAT  GCCTTCGACG  TG                                   812
```

( 2 ) INFORMATION FOR SEQ ID NO:2:

( i ) SEQUENCE CHARACTERISTICS:
      ( A ) LENGTH: 116 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:2:

```
Met Arg Gln Ile Pro Val Asp Thr Ser Ala Ala Thr Val Met Val Ala
 1               5                   10                  15

Lys Thr Pro Glu Pro Lys Val Lys Asp Arg Arg Thr Gly Glu Leu Ala
             20                   25                  30

Val Asp Ala Glu Thr Gly Ala Lys Leu Met Thr Val Asn Val Met Phe
         35                   40                  45

Ala Ala Asn Asp Glu Val Glu Ile Leu Ser Val Thr Val Pro Glu Thr
     50                   55              60

Gly Ile Ser Gly Glu Leu Ala Met Gly Thr Pro Val Ala Leu Thr Gly
 65                   70                   75                  80

Leu Ile Ala Arg Pro Trp Glu Asn Glu Phe Asn Gly Gln Lys Arg His
             85                   90                  95

Gly Ile Ala Phe Arg Ala Val Ala Val Thr Ser Leu Thr Ala Ala Gly
            100                  105                 110

Ser Lys Ala Ala
        115
```

REGULATORY NUCLEIC ACID SEQUENCES AND USES IN ACTINOMYCETES

The present invention relates to a new nucleic acid sequence, to vectors for its expression and to its use in fermentation processes in actinomycetes.

Actinomycetes are branched filamentous Gram-(+) bacteria. Among actinomycetes, streptomycetes represent the largest family. Streptomycetes are spore-forming filamentous bacteria which live naturally in the soil under strictly aerobic conditions.

Actinomycetes, and streptomycetes in particular, are of great importance from an industrial standpoint. In particular, they possess the feature of producing a wide variety of secondary metabolites (Demain, Biology of Actinomycetes 88, Okami (Eds), Tokyo, Japan scientific societies press, 1988, p. 19–25). These metabolites can have very different structures and biological properties (herbicides, anticancer agents, anthelmintics, anabolic agents, antibiotics, and the like). The best known of these metabolites are antibiotics (chemical substances produced by an organism and having a deleterious effect on other organisms). Streptomyces are currently the source of 70% of industrially produced antibiotics. The structural diversity of the antibiotics synthesized is not to be found in any other bacterial genus. Thus, almost all types of structure are represented: β-lactams (e.g. ampicillin), polypeptide antibiotics (e.g. streptogramins), aminoglycoside antibiotics (e.g streptomycin, kanamycin, and the like), macrolides (e.g. erythromycin, spiramycin, and the like) or alternatively cyclines (e.g. tetracycline), and the like.

For these reason, it is especially advantageous to be able to have tools (vectors, promoters, and the like) at one's disposal enabling these microorganisms to be manipulated genetically. Such tools would make it possible, in effect, to modify the levels of synthesis of these metabolites, or to prepare synthesis intermediates or derivatives of these metabolites, and the like. Such tools would also make it possible to make these microorganisms manufacture recombinant products, in particular heterologous proteins, according to genetic engineering techniques.

In this connection, Patent Application No. EP 350,341 describes vectors derived from plasmid pSAM2 having very advantageous properties. Thus, these vectors are capable of integrating in a site-specific manner in the genome of actinomycetes, and possess a broad host range and high stability. Moreover, they may be used for transferring nucleic acids into actinomycetes and expressing these nucleic acids therein. However, these vectors possess some drawbacks, which lie, in particular, in their low copy number per cell, and in the absence of means of controlling the copy number. Thus, pSAM2 and its derivatives generally integrate on the basis of a single copy per chromosome.

The present invention supplies a solution to this problem, by providing tools capable of improving the conditions of industrial use of the vectors derived from pSAM2. The present invention describes, in effect, a gene whose expression product leads to the appearance, from integrated forms, of replicative free forms of plasmid pSAM2 or of vectors derived from the latter. This has the effect of increasing the copy number of pSAM2 or its derivatives, since the free forms are present in a high copy number per cell.

The present invention also describes cassettes for the expression of this gene, vectors containing it and their use for inducing the appearance of free copies of pSAM2 or integrative vectors derived from the latter.

The Applicant has, in effect, isolated, sequenced and characterized a region of plasmid pSAM2 capable of inducing the appearance of replicative free copies of pSAM2 or its derivatives. The Applicant has also shown that this region could be used in cis (on the same vector) or in trans (not on the same vector) to act on pSAM2 or its derivatives. The sequence of this region is presented in the sequence SEQ ID NOS:1 and 2. More specifically, this region and its functional role were demonstrated by studying variants of plasmid pSAM2: on the one hand pSAM2(B2) originating from S. ambofaciens ATCC 15154 for which no free form is observed, and on the other hand pSAM2 (B3) and pSAM2 (B4) originating from other S. ambofaciens strains for which the free form is observed with the integrated form. This study enabled two different point mutations to be characterized (those of pSAM2 (B3) and that of pSAM2 (B4), both localized in the promoter region controlling the expression of a pSAM2 gene (see SEQ ID NOS:1 and 2. These mutations lead to the appearance of the free form of pSAM2 (B3) and of pSAM2 (B4). This gene was then cloned and sequenced, and its capacity to cause the appearance of the free form of plasmids derived from pSAM2 from the integrated copy was demonstrated.

A first subject of the invention hence lies in a nucleic acid sequence comprising all or part of the sequence SEQ ID NOS:1 and 2 or of a variant of the latter.

For the purposes of the present invention, the term variant denotes any sequence differing from the sequence SEQ ID NOS:1 and 2 as a result of the degeneracy of the genetic code, as well as any sequence which hybridizes with these sequences or fragments of the latter and whose product possesses the stated activity. These variants may be obtained from SEQ ID No. 1 by any technique known to a person skilled in the art, in particular mutation, deletion, substitution, addition, hybridization and the like. Hybridizations may be carried out under conventional conditions of stringency (Maniatis et al., see General techniques of molecular biology) or, preferably, under conditions of high stringency. The capacity of the variants to induce the appearance of replicative free forms of pSAM2 or its derivatives may be determined on an actinomycete strain containing such a plasmid in integrated form (for example on the strain ATCC 15154), by transfecting the said variant into the strain under conditions permitting its expression, and verifying the appearance of the free forms (see examples).

Another subject of the invention relates to any cassette for the expression of the sequence SEQ ID No. 1 or of a variant of the latter as defined above, comprising the said sequence or variant under the control of a constitutive or regulated promoter.

The use of a constitutive promoter is especially advantageous when the cassette is used in tans to induce free forms of an integrated plasmid. In this case, the cells containing the integrated form of the plasmid are transfected with the expression cassette to induce the appearance of replicative free forms, making it possible, for example, to isolate and/or purify the plasmid.

The use of a regulated promoter is especially advantageous when the cassette is used in cis (on the vector derived from pSAM2 itself), for example in an industrial fermentation process. In this case, the whole of the proliferation and growth phase of the cell is performed without expression of the gene of the invention, that is to say with a single copy of the plasmid per chromosome, and, for the production phase (of a recombinant product, of a gene for the biosynthesis or regulation of the synthesis of a metabolite, and the like), the regulated promoter is induced, bringing about the appearance of several free copies of the plasmid and thus an enhanced production activity. This mode of implementation is especially advantageous when the vector derived from pSAM2 carries heterologous sequences whose presence in several number of copies may be toxic to the cells and/or affect their growth.

Among constitutive promoters which can be used in the context of the present invention, mention may be made more especially of any constitutive promoter which is functional in actinomycetes, such as, for example, the promoter of the ermE gene or a variant of the latter (Bibb et al., Gene 41 (1986) E357), the p14 promoter of phage I19 of *S. ghanaensis* (Labes et al., Sixth DFGWT/AFAST, 27–30/11/92), or any fragment containing a promoter region of a ribosomal operon of *S. ambofaciens* (Pernodet et al., Gene 79 (1989) 33).

Among regulable promoters which can be used in the context of the present invention, mention may be made more especially of any regulable promoter which is functional in actinomycetes. These can comprise promoters induced specifically by an agent introduced into to the culture medium, such as, for example, the thiostrepton-inducible promoter tipA (Murakami et al., J. Bactt., 171 (1989) 1459), or thermoinducible promoters such as that of the groEL genes, for example (Mazodier et al., J. Bact. 173 (1991) 7382). They can also comprise an actinomycetes promoter which is specifically active in the late phases of the proliferation cycle of actinomycetes, such as, for example, certain promoters of genes of the secondary metabolism (genes for the production of antibiotics, in particular).

Another subject of the invention relates to the use of the sequences of the invention as defined above, or of cassettes containing them, for inducing the appearance of free copies of vectors which are derived from pSAM2 and integrated in an actinomycete.

As stated above, this use may be performed in cis (the gene or cassette being carried by the integrative vector derived from pSAM2) or in trans (the gene or cassette being on another vector or even introduced directly as such).

The integrative vectors derived from pSAM2 as mentioned above are vectors comprising at least the elements of pSAM2 needed for integration, excision and replication. More especially, these vectors hence comprise at least the attP and int regions as described in Application EP 350,341, the Xis gene, the repSA gene and the origin of replication (ori). These different regions are shown on the map of plasmid pSAM2 given in FIG. 1, on which some restriction sites enabling these regions to be extracted also appear.

Advantageously, the integrative vectors derived from pSAM2 also comprise a recombinant DNA sequence coding for a desired product. The latter can be a peptide, polypeptide or protein of pharmaceutical or agri-foodstuffs importance. In this case, the system of the invention makes it possible to increase the copy number of this sequence per cell, and hence to increase the levels of production of this product and thus to increase the yields of the preparation process. The desired product can also be a peptide, polypeptide or protein participating in the biosynthesis (synthesis, degradation, transport or regulation) of a metabolite by the actinomycete strain in question. In this case, the system of the invention makes it possible to increase the copy number of this sequence per cell, and hence to increase the levels of production of this product, and thus either to increase the levels of production of the metabolite, or to block the biosynthesis of the metabolite, or to produce derivatives of the metabolite.

The sequences of the invention may thus be used in any actinomycete, in the genome of which pSAM2 vectors or its derivatives are capable of integrating. In particular, they may be used in fermentation processes involving strains of Streptomyces, of mycobacteria, of bacilli, and the like. As an example, there may be mentioned the strains *S. pristinaespiralis* (ATCC 25486), *S. antibioticus* (DSM 40868), *S. bikiniensis* (ATCC 11062), *S. parvulus* (ATCC 12434), *S. glauescens* (ETH 22794), *S. actuosus* (ATCC 25421), *S. coelicolor* (A3(2)), *S. ambofaciens*, *S. lividans*, *S. griseofuscus*, *S. limosus*, and the like (see also Smokvina et al., Applications of the integrated plasmid pSAM2, GIM90, Proceedings, Vol. 1, p. 403–407).

Vectors derived from pSAM2 containing the elements described above may be constructed by a person skilled in the art on the basis of his general body of knowledge and the teachings of the present application (see also General techniques of molecular biology), The sequences of the invention are most especially suitable for use in an industrial process for the production of antibiotics (spiramycin, streptogramins, β-lactams, and the like, the genes for which are described in Applications EP 346,000 and PCT/FR93/00923, in particular.

The present invention will be described more fully by means of the examples which follow, which are to be considered to be illustrative and non-limiting.

LEGEND TO THE FIGURES

FIG. 1. Restriction map of plasmid pSAM2

Figure 2:
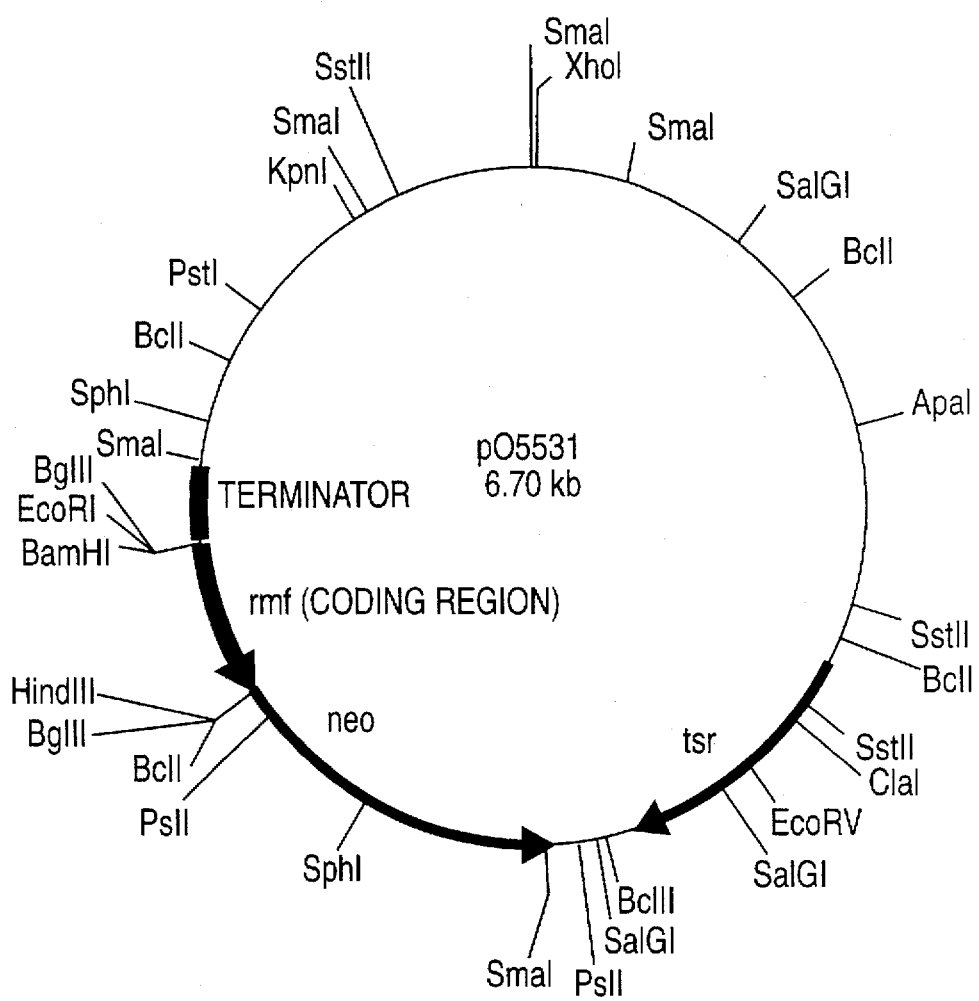

FIG. 2. Restriction map of the vector pOS531

Figure 3:
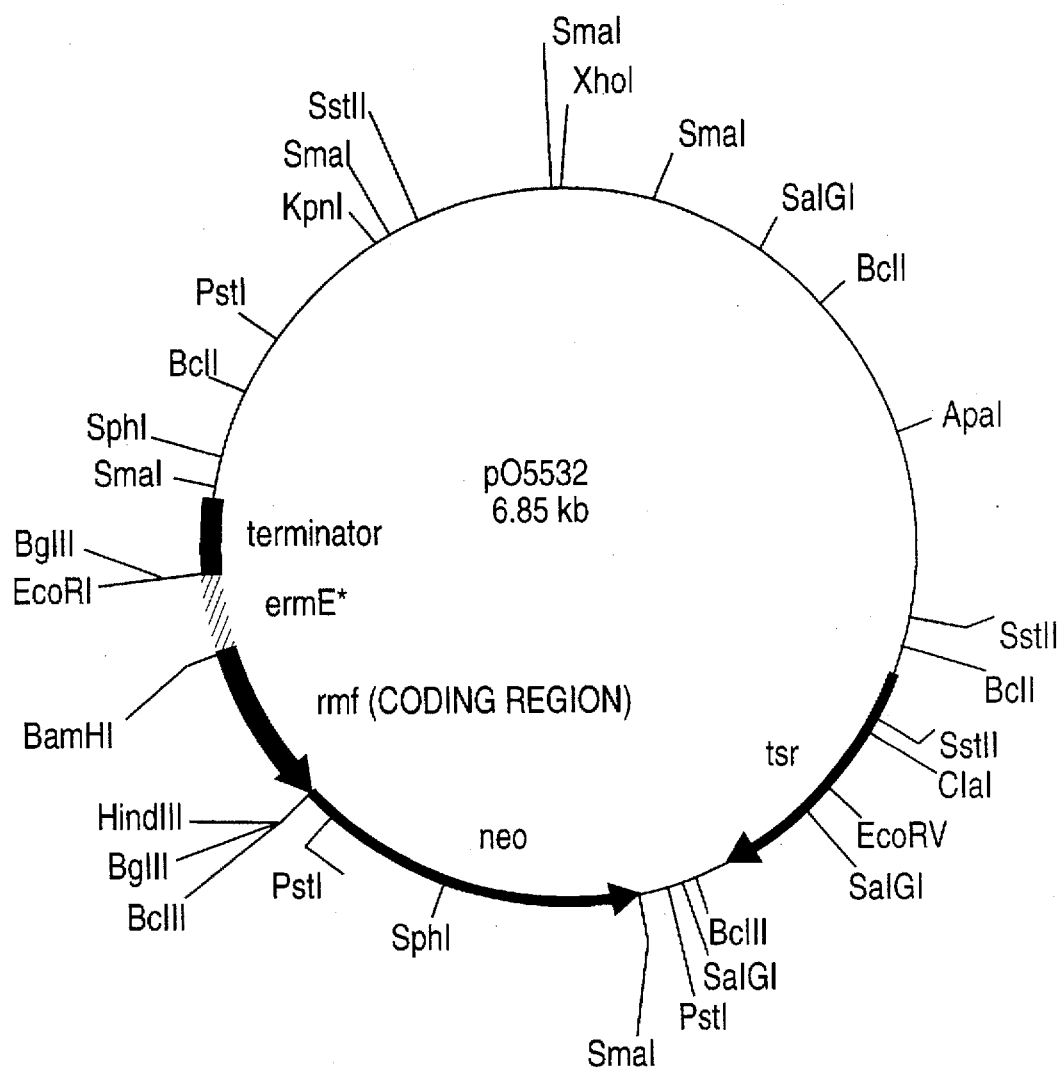

FIG. 3. Restriction map of the vector pOS532

Figure 4:
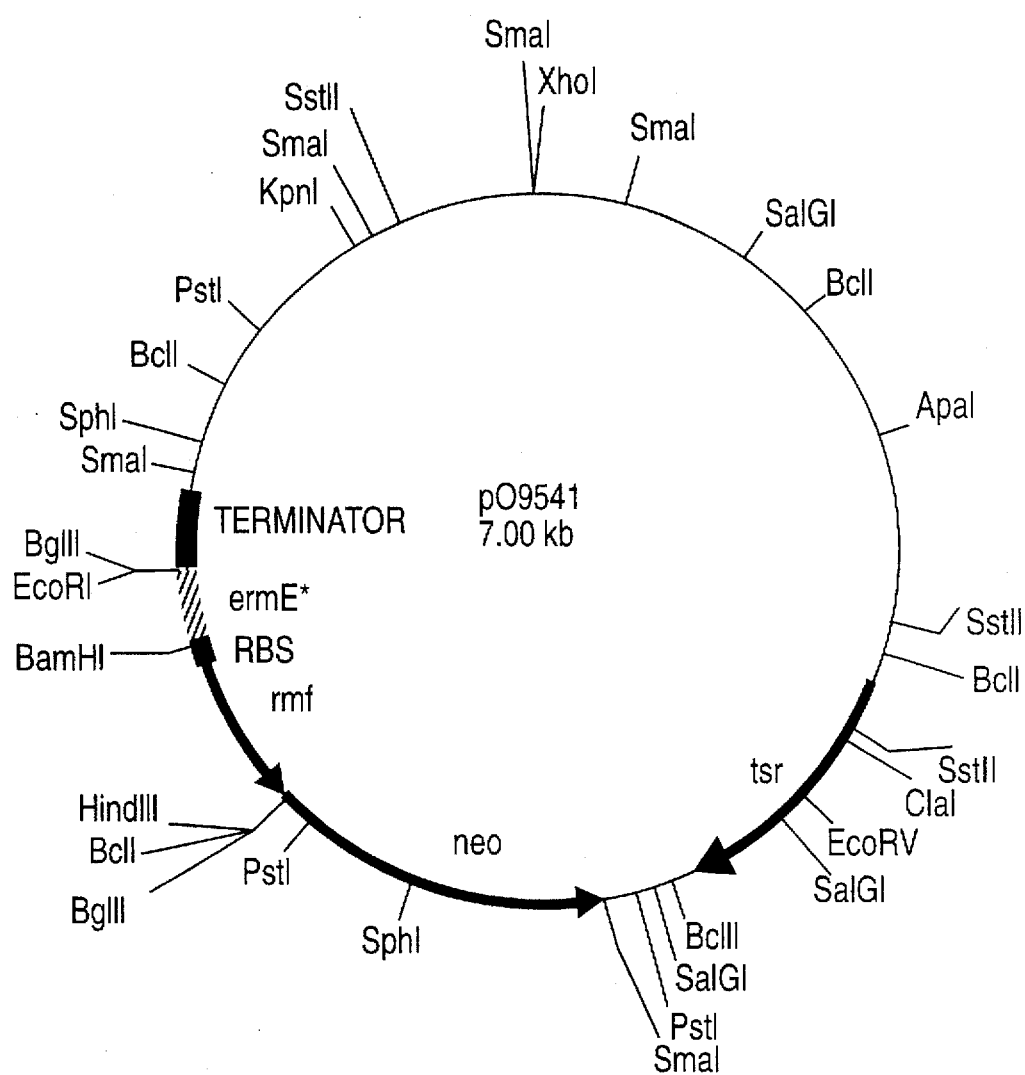

FIG. 4. Restriction map of the vector pOS541

Figure 5:
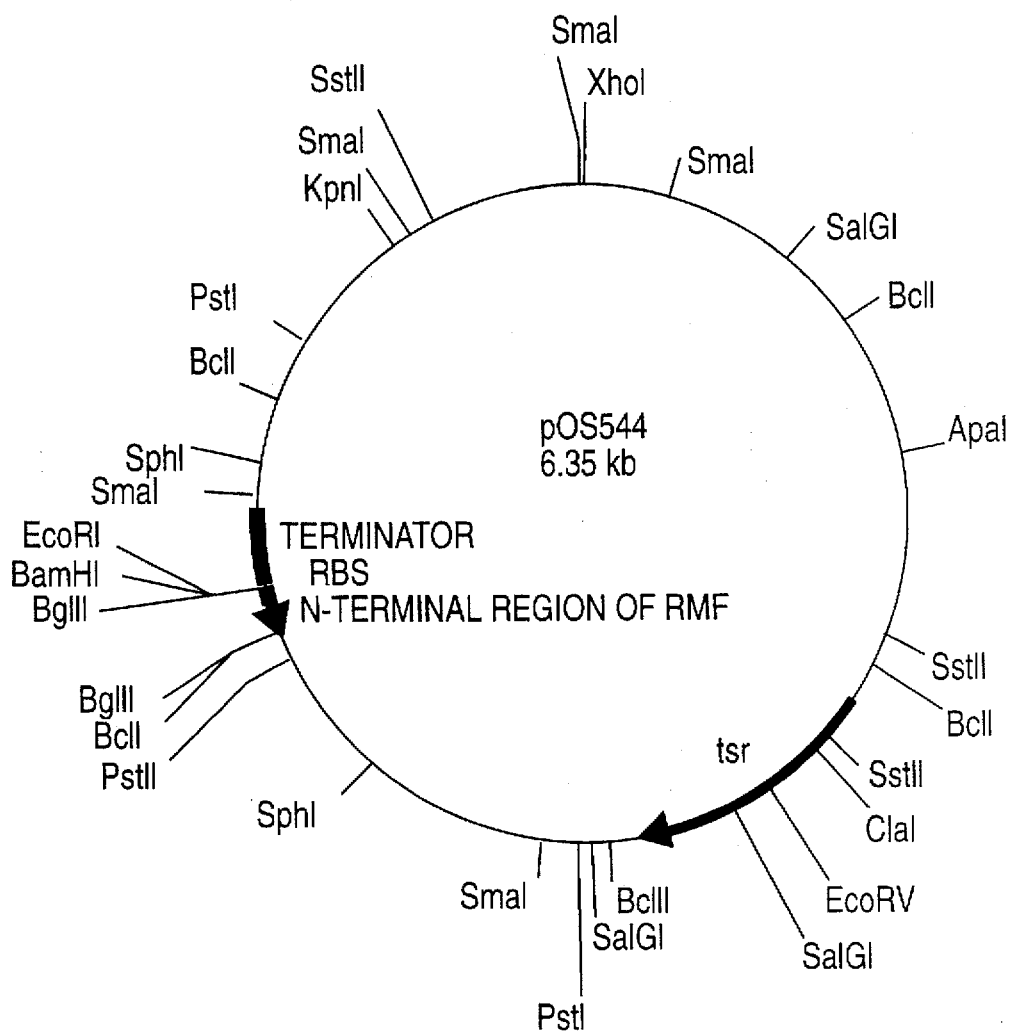

FIG. 5. Restriction map of the vector pOS544

Figure 6:
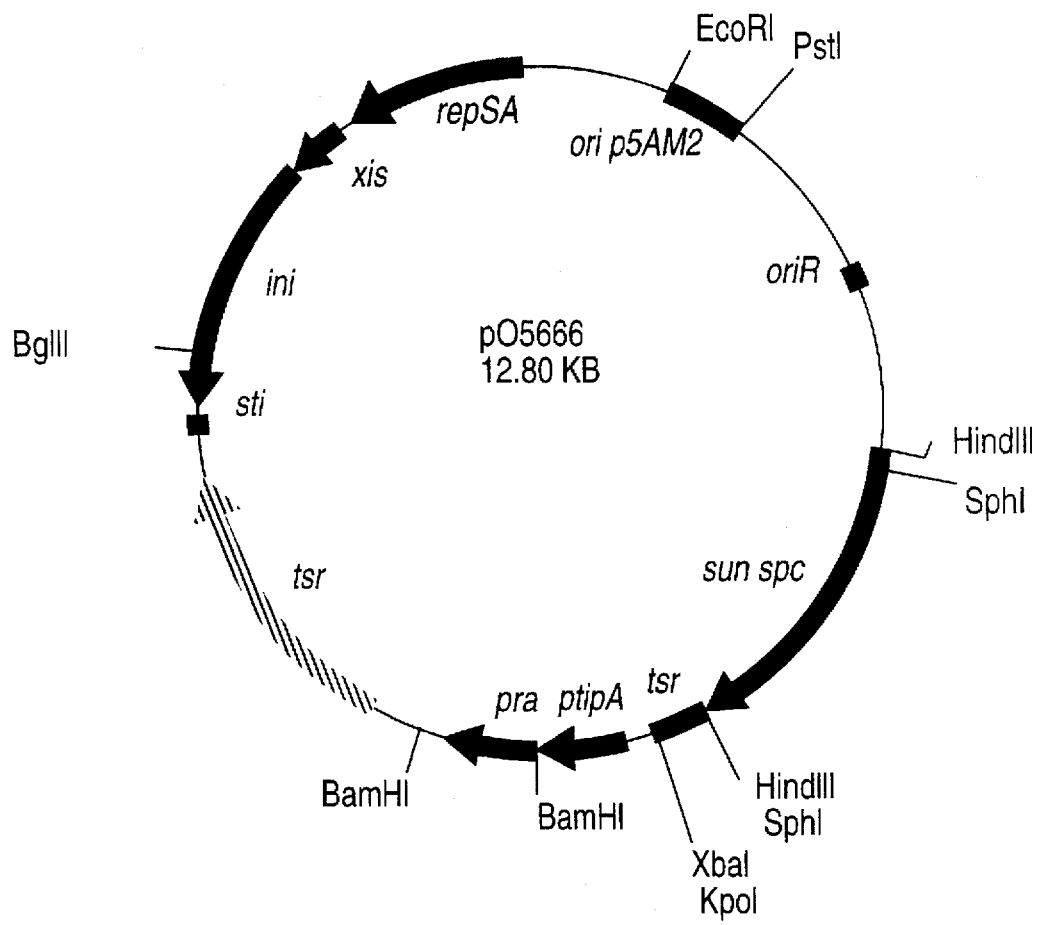

FIG. 6. Restriction map of the vector pOS666. This vector is constructed from plasmid pPM927 (Smokvina et al., gene 94 (1990) 53) by insertion of the rmf gene (also designated pra) and the origin of replication of pSAM2: tsr: thiostrepton resistance gene; stm/spc: streptomycin/spectinomycin resistance gene; oriR: E. coli origin of replication; oripSAM2: origin of replication of pSAM2; ter: transcription terminator.

FIG. 7. Activity of the vectors.

GENERAL TECHNIQUES OF MOLECULAR BIOLOGY

The methods traditionally used in molecular biology, such as preparative extractions of plasmid DNA, centrifugation of plasmid DNA in a caesium chloride gradient, agarose or acrylamide gel electrophoresis, purification of DNA fragments by electroelution, protein extractions with phenol or phemnol/chloroform, ethanol or isopropanol precipitation of DNA in a saline medium, transformation in *Escherichia coli*, and the like, are well known to a person skilled in the art and are amply described in the literature [Maniatis T. et al., "Molecular Cloning, a Laboratory Manual", Cold Spring Harbor Laboratory, Cold Spring Harbor, N.Y., 1982; Ausubel F. M. et al. (eds), "Current Protocols in Molecular Biology", John Wiley & Sons, New York 1987].

Plasmids of the pBR322 or pUC type and phages of the M13 series are of commercial origin (Bethesda Research Laboratories).

For ligation, the DNA fragments may be separated according to their size by agarose or acrylamide gel electrophoresis, extracted with phenol or with a phenol/chloroform mixture, precipitated with ethanol and then incubated in the presence of phage T4 DNA ligase (Biolabs) according to the supplier's recommendations.

The filling-in of 5' protruding ends may be performed with the Klenow fragment of E. coli DNA polymerase I (Biolabs) according to the supplier's specifications. The destruction of 3' protruding ends is performed in the presence of phage T4 DNA polymerase (Biolabs) used according to the manufacturer's recommendations. The destruction of 5' protruding ends is performed by a controlled treatment with S1 nuclease.

Mutagenesis directed in vitro by synthetic oligodeoxynucleotides may be performed according to the method developed by Taylor et al. [Nucleic Acids Res. 13 (1985) 8749–8764] using the kit distributed by Amersham.

The enzymatic amplification of DNA fragments by the so-called PCR [Polymerase-catalyzed Chain Reaction, Saiki R. K. et al., Science 230 (1985) 1350–1354; Mullis, K. B. and Faloona F. A., Meth. Enzym. 155 (1987) 335–350] technique may be performed using a "DNA thermal cycler" (Perkin Elmer Cetus) according to the manufacturer's specifications.

Verification of the nucleotide sequences may be performed by the method developed by Sanger et al. [Proc. Natl. Acad. Sci. USA, 74 (1977) 5463–5467] using the kit distributed by Amersham.

EXAMPLES

Example 1

Cloning and sequencing of the sequence SEQ ID No. 1

The free form of pSAM2 (B2) is not observed in *S. lividans* TK24 (Hopwood et al., J. Gen. Microbiol. 129 (1983) 2257), only the integrated form is observed. With pSAM2 (B3), the free form of the plasmid coexists with the integrated form. Hybrid plasmids were from pSAM2 (B3) in which different regions were replaced by the equivalent regions originating from pSAM2 (B2). This enables it to be shown that the mutation enabling pSAM2 (B3) to exist in free form was localized in a 2-kb KpnI restriction fragment. The sequence of this KpnI fragment was determined for pSAM2 (B2) and pSAM2 (B3). A single nucleotide differs between these two sequences: a G/C pair in pSAM2 (B2) is replaced by an A/T pair in pAM2 (B3). Sequence analysis showed that this mutation occurred upstream of an open reading frame which extended further than the KpnI site. The sequence of this open reading frame was determined; it is presented in the sequence SEQ ID No. 1. This open reading frame, designated rmf (or pra), is located between the korSA and traSA genes. The mutation causes the disappearance of a recognition site for the restriction enzyme ApaLI (recognition site: 5'GTGCAC 3'). This site is present in pSAM2 (B2) but absent in pSAM2 (B3).

The sequence SEQ ID No. 1 also comprises 100 bp upstream of the coding region, comprising a protion of the promoter (residues 1 to 101) and the 5' non-coding but transcribed region (residues 102 to 154) carrying, in particular, the ribosome binding site (RBS).

In the mutant pSAM2 (B4, for which the free form can be observed, the ApaLI site is still present, indicating that the mutation is not localized at the same place as in pSAM2 (B3). The sequence of pSAM2 (B4) for the corresponding region showed that the sequences of pSAM2 (B2) and of pSAM2 (B4) differed by one nucleotide. This mutation was localized 8 nucleotides upstream of the mutation detected in pSAM2 (B3). Thus, in two independent cases, the presence of the free form of pSAM2 (B3) and pSAM2 (B4), which coexists with the integrated form, is due to a point mutation upstream of a pSAM2 gene. These two independent mutations are both located in a region shown by messenger RNA analysis experiments to constitute the promoter of this gene.

Example 2

Construction of cassettes and vectors for the portion of the sequence SEQ ID No. 1

Several constructions were carried out using the following promoters and plasmids:

Modified ermE promoter (ermE*). The modified ermE promoter used corresponds to the promoter described by Bibb et al. cited above, possessing a deletion of 3 nucleotides (bases 252–254, FIG. 2 of Bibb et al. cited above). This modified promoter gives a strong and constitutive expression. It was isolated in the form of a 275-bp KpnI-BamHI fragment.

tipA promoter. This promoter (Murakami et al. cited above) is present in plasmid pPM927 (Smokvina et al., Gene 94 (1990) 53). This is induced specifically in the presence of thiostrepton.

Plasmids pIJ486 and pIJ487. These two plasmids have been described by Ward et al. (Mol. Gen. Genet. 203 (1986) 468). These plasmids alone have no influence on the status (free or integrated) of pSAM2.

2.1. Construction of the vector pOS531

The vector pOS531 was constructed by cloning the coding portion of the rmf gene (residues 155 to 505 of the sequence SEQ ID No. 1) at the BamHI-HindIII sites of plasmid pIJ487. This vector hence carries the naked rmf gene (without expression signal or 5' non-coding region). A map of this vector is given in FIG. 2.

2.2. Construction of the vector pOS532

The vector pOS532 was constructed by cloning the 275-bp fragment carrying the modified ermE promoter at the EcoRI-BamHI sites of the vector pOS531. This vector hence carries the naked rmf gene under the control of the modified ermE promoter (FIG. 3).

2.3. Construction of the vector pOS541

The vector pOS541 was constructed in 2 steps:

cloning of a fragment containing the coding portion of the rmf gene and the 5' non-coding region (residues 102 to 505 of the sequence SEQ ID No. 1) at the BamHI-HindIII sites of plasmid pIJ487, addition of the 275-bp fragment carrying the modified ermE promoter at the EcoRI-BamHI sites of the vector obtained above.

This vector hence carries the rmf gene provided with its 5' non-coding region, under the control of the modified ermE promoter (FIG. 4).

2.4. Construction of the vector pOS544

The vector pOS544 carries an rmf gene deleted in its 3' portion (residues 102 to 276 of the sequence SEQ ID No. 1 are present). It was constructed by cloning this region in the form of a BamHI-BspHI fragment (BspHI end treated with the Klenow fragment of *E. coli* DNA polymerase I) into the BamHI-HindIII sites of plasmid pIJ487 (HindIII end treated with the Klenow fragment of *E. coli* DNA polymerase I). The vector pOS544 hence carries the 5' portion of the rmf gens (5' non-coding region +5' coding region), which portion lacks, however, its promoter. A map of this vector is given in FIG. 5.

Example 3

Appearance of replicative free forms of integrative vectors derived from pSAM2due to the expression product of the rmf gene This example shows that the overexpression of the gens SEQ ID No. 1 can cause the appearance in free form of an integrated copy of pSAM2.

3.1. Direct evidence for the role of replication activator played by rmf may be obtained by causing, by expression of rmf, the appearance in free form of an integrated copy of pSAM2(B2). The fact that pSAM2(B2) possesses an additional ApaLI site relative to pSAM2(B3) enables it to be verified simply by observation of the ApaLI digestion profile that the free plasmid is indeed pSAM2(B2).

3.2. The activity of the sequence SEQ ID No. 1 was also demonstrated by transformation of *S. lividans* carrying an integrated copy of pSAM2(B2) with the different vectors described above, followed by a search for free forms. To this end, *S. lividans* containing plasmid pSAM2(B2) was transformed by the protoplast technique with the different vectors described in Example 2. The plasmid DNA or total cellular DNA is extracted from a stationary-phase culture of the transformed clones. The plasmid DNA is digested with the enzyme ApaLI and the digestion fragments separated by agarose gel electrophoresis. Observation of the restriction profile reveals whether or not free copies of pSAM2(B2) are present. These results are then confirmed by experiments involving hybridization of the total DNA with a pSAM2probe.

Results obtained are presented in FIG. 7.

These results show that pOS541, which contains the modified ermE promoter, the untranslated region upstream of rmf with the ribosome binding site and the rmf coding frame, causes the appearance of replicative free forms of pSAM2(B2). As expected, no effect is observed with a vector containing only the rmf coding portion (pOS531), or with a vector containing modified ermE and the coding portion of rmf but no ribosome binding region (pOS532). No effect is observed with a vector carrying a deletion in the 3' portion of rmf (pOS544).

The same type of effect is obtained when the cassette permitting inducible expression of rmf is localized on the plasmid for which it is desired to cause the appearance of free forms (vector pOS666, FIG. 6).

These results collectively provide a clear demonstration that the sequence of the invention is capable of inducing, in cis or in trans, the appearance of free forms of vectors derived from pSAM2.

We claim:

1. An isolated nucleic acid comprising all or part of the sequence SEQ ID NO. 1 or a variant of the latter, which sequence or variant of said sequence is capable of inducing the appearance of replicative free copies of pSAM2 or its derivatives and wherein said sequence or variant of said sequence is under the control of a promoter functional in actinomycetes wherein the promoter is a heterologous constitutive promoter or a heterologous regulated promoter.

2. An expression cassette comprising an isolated nucleic acid comprising all or part of the sequence SEQ ID NO. 1 or a variant of the latter, which sequence or variant of said sequence is capable of inducing the appearance of replicative free copies of pSAM2 or its derivatives and wherein said sequence or variant of said sequence is under the control of a constitutive or regulated promoter functional in actinomycetes.

3. The expression cassette according to claim 2, wherein the constitutive promoter is chosen from the promoter of the ermE gene or a variant of the latter, the p14 promoter of phage I19 of *S. ghanaensis*, or any fragment containing a promoter region of a ribosomal operon of *S. ambofaciens*.

4. The expression cassette according to claim 2, wherein the regulated promoter is chosen from promoters induced specifically by an agent introduced into the culture medium.

5. The expression cassette according to claim 2, wherein the regulated promoter is chosen from actinomycetes promoters which are specifically active in the late phases of the proliferation cycle of actinomycetes.

6. The expression cassette as claimed in claim 4, wherein the promoter is the thiostrepton-inducible promoter tipA.

7. The expression cassette as claimed in claim 4, wherein the promoter is a thermoinducible promoter.

8. The expression cassette as claimed in claim 7, wherein the promoter is from groEL genes.

9. The expression cassette as claimed in claim 5, wherein the actinomycetes promoter is a promoter of genes of secondary metabolism.

10. The expression cassette as claimed in claim 5, wherein the actinomycetes promoter is a promoter of genes for the production of antibiotics.

11. A method for inducing the appearance of free copies of vectors derived from pSAM2, comprising the following steps:

(a) isolating at least part of the sequence SEQ ID NO:1 or a variant of the sequence;

(b) inserting at least part of the sequence or a variant of the sequence into an expression cassette;

(c) transfecting the expression cassette into a host strain under conditions permitting expression of the sequence.

12. The method as claimed in claim 11, wherein the expression cassette is inserted into a vector before transfection into a host strain.

13. The method as claimed in claim 12, wherein the vector is derived from pSAM2.

14. The method as claimed in claim 11, wherein the host strain is actinomycete.

15. The method as claimed in claim 14, wherein the actinomycete is selected from the group consisting of Streptomyces, mycobacteria, and bacilli.

16. The method of claim 15 further comprising the step of producing an antibiotic.

* * * * *